(12) United States Patent
Kozak et al.

(10) Patent No.: US 6,774,121 B1
(45) Date of Patent: Aug. 10, 2004

(54) PHOSPHOLIPID PRODRUGS OF ANTI-PROLIFERATIVE DRUGS

(75) Inventors: Alexander Kozak, Rehovot (IL); Israel Shapiro, Ramla (IL); Marina Vinnikova, Ramla (IL); Leonid Ershov, Beit Shemesh (IL); Alexander Senderikhin, Ashdod (IL); Oran Ayalon, Ganel Yohanan (IL)

(73) Assignee: D-Pharm, Ltd., Rehovot (IL)

( * ) Notice: Subject to any disclaimer, the term of this patent is extended or adjusted under 35 U.S.C. 154(b) by 49 days.

(21) Appl. No.: 10/088,160

(22) PCT Filed: Sep. 13, 2000

(86) PCT No.: PCT/IL00/00562

§ 371 (c)(1),
(2), (4) Date: Mar. 13, 2002

(87) PCT Pub. No.: WO01/19320

PCT Pub. Date: Mar. 22, 2001

(30) Foreign Application Priority Data

Sep. 14, 1999 (IL) .................................................. 131887

(51) Int. Cl.$^7$ ...................... A61K 31/661; C07F 9/6512
(52) U.S. Cl. ............................ 514/49; 514/50; 514/51; 514/249; 536/26.8; 544/243; 544/244
(58) Field of Search ........................... 544/244; 514/49, 514/249

(56) References Cited

U.S. PATENT DOCUMENTS

| | | |
|---|---|---|
| 4,772,594 A | 9/1988 | Hashimoto et al. |
| 5,149,794 A | 9/1992 | Yatvin et al. |
| 5,411,947 A | 5/1995 | Hostetler et al. |
| 5,543,389 A | 8/1996 | Yatvin et al. |
| 6,028,066 A | 2/2000 | Unger |
| 6,077,837 A | 6/2000 | Kozak |

FOREIGN PATENT DOCUMENTS

| | | |
|---|---|---|
| WO | 9000555 | 1/1990 |
| WO | 9116920 | 11/1991 |
| WO | 9300910 | 1/1993 |
| WO | 9422483 | 10/1994 |

*Primary Examiner*—Richard L. Raymond
(74) *Attorney, Agent, or Firm*—Davidson, Davidson & Kappel, LLC

(57) ABSTRACT

The invention discloses prodrugs comprising anti-proliferative drugs covalently linked, via bridging group, to a phospholipid moiety such that the active species is preferentially released, preferably by enzymatic cleavage, at the required site of action. The invention further discloses pharmaceutical compositions said prodrugs and the uses thereof for the treatment of diseases and disorders related to inflammatory, to degenerative or atrophic conditions, and to uncontrolled cell growth. FIG. 1 depicts a graph of animal survival during the course of an experiment wherein mice were i.p. transplanted with 11210 mouse leukemia cells and then treated with vehicle only (squares), MTX (triangles) or molar equivalent dose of DP-MTX071 (circles) according to the regiment described example in Example 11.

29 Claims, 1 Drawing Sheet

PHOSPHOLIPID PRODRUGS OF ANTI-PROLIFERATIVE DRUGS

FIELD OF THE INVENTION

The present invention relates to prodrugs of anti-proliferative agents comprising a phospholipid moiety covalently linked, via a bridging group, to an anti-proliferative agent, such that the active species is preferentially released, preferably by enzymatic cleavage, at the required site of action.

The invention further relates to pharmaceutical compositions comprising said prodrugs and to the use thereof for the treatment of diseases and disorders related to inflammatory, degenerative or atrophic conditions and to uncontrolled cell growth.

BACKGROUND OF THE INVENTION

Anti-proliferative drugs, also known as anti-metabolites, act by inhibiting crucial metabolic processes and are commonly used in the treatment of diseases involving abnormal cell proliferation, such as tumors. Many anti-proliferative drugs are also useful as anti-inflammatory agents, exerting their effect by suppressing local or even systemic inflammatory responses mediated by the immune system However, the utility of these drugs is severely hampered by their excessive toxicity and adverse side effects on healthy cells of the treated patient.

Methotrexate (MTX) is an effective anti-proliferative drug commonly used in cancer therapy. MTX is also known as a leading anti-inflammatory drug, and is currently the main drug used in the treatment of rheumatoid arthritis (RA). It is the drug of first choice for treating children with recalcitrant juvenile RA.

Methotrexate is an analogue of dihydrofolate that inhibits the enzyme dihydrofolate reductase (DHFR), thus depleting intracellular tetrahydrofolate ($FH_4$) which is an essential co-factor required for the de novo synthesis of purine nucleotides.

Another anti-metabolite widely used in cancer chemotherapy is the pyrimidine analog fluorodeoxyuridine (FUdR). FUdR is converted in vivo into fluorodeoxyuridylate (F-dUMP) which is an analog of the al substrate dUMP and irreversibly inhibits thymidylate synthase.

MTX and FUdR are valuable drugs in the treatment of many rapidly growing tumors, however, their use is limited by the frequency and severity of side effects. Unwanted side effects include toxicity to all rapidly dividing normal cells, such as stem cells in the bone marrow, epithelial cells of the intestinal tract, etc. Folic acid antagonists are also toxic to developing embryos. Treatment with MTX is especially problematic in patients having chronic debilitating inflammatory diseases that require prolonged therapy, such diseases as rheumatoid arthritis, asthma, dermatological diseases such as psoriasis and gastrointestinal inflammation such as Crohn's disease. These patients may suffer from induced nephrotoxicity, due to precipitation of the drug or its metabolites in the renal tubes, and from hepatic fibrosis and cirrhosis.

Another major problem in chemotherapy, which is particularly relevant in the case of anti-metabolites, is inherent or acquired resistance of tumors to cytotoxic drugs. For example, development of resistance to MTX frequently follows prolonged exposure to this drug. Resistance may be due to new mutations induced by the clinical treatment or to positive selection, by the treatment regimen, of pre-existing resistant mutant cell. Known mechanisms for development of resistance involve impaired transport of MTX into cells, e.g. by mutations in the Reduced Folates Carrier (RFC), over expression of the target enzyme DHFR, or mutations in the enzyme responsible for polyglutamination of reduced folates (FPGS).

A more severe problem in the clinic is the phenomenon of multi-drug resistance (MDR), which is a resistance to a broad spectrum of structurally unrelated cytotoxic drugs. MDR is mediated by membranal "pumps" which actively expel chemotherapeutic drugs from the tumor cells. Two drug pumps commonly found in cancer are P-glycoprotein (P-gp) and multidrug resistance-associated protein (MRP). MDR significantly limits the efficacy of many cancer chemotherapy regimens-and is a major factor in the failure of cancer chemotherapy.

It would, therefore, be most advantageous to have drug derivatives that are targeted or selectively active in the diseased cells rather than in the healthy cells, thus reducing undesirable side effects. It would also be desirable to generate new anti-proliferative agents that overcome drug-resistance, as well as agents that are active as cytotoxic drugs but lack or have a reduced ability to provoke MDR phenotype.

The use of prodrugs to impart desired characteristics such as increased bioavailability or increased site-specificity for known drugs is a recognized concept in the state of the art of pharmaceutical development. The use of various lipids in the preparation of particular types of prodrugs is also known in the background art In none of those instances are the prodrugs able to achieve preferential accumulation of an anti-proliferative drug within the diseased cells of the organ, by activation with intracellular lipases. Rather, the prodrugs enable the drug to be transported to a specific site, or to be released within a specific organ, as in the case of the phospholipid pro drugs of salicylates and non-steroidal anti-inflammatory drugs disclosed in International Patent Application WO 91/16920 which, taken orally, protect the gastric mucosa and release the active principle in the gut.

In other examples of phospholipid prodrugs, the formulation of the prodrugs into liposomes or other micellar structures is the feature that enables their preferential uptake, for instance by liver cells or by macrophages as in the case of the phospholipid conjugates of antiviral drugs disclosed in International patent applications WO 93/00910 and WO 90/00555.

U.S. Pat. No. 5,411,947 discloses a method of converting a drug to an orally available form by covalently bonding a lipid to the drug. It discloses a lipid prodrug of 5-fluorouridine, but differs from the present invention in that the drug is attached to the lipid at the $R^3$ position.

U.S. Pat. No. 4,772,594 discloses prodrugs containing 5-Fluorouracil, but differs from the present invention in that the drug is attached to cholesterol.

U.S. Pat. Nos. 5,149,794 and 5,543,389 disclose covalent polar lipid-drug conjugates to facilitate the entry of drugs into cells at pharmokinetically useful levels. In contrast to the present invention, the disclosed prodrugs are directed to certain intracellular structures and organelles due to the existence of the polar lipid carrier, and drug release from the lipid conjugate is not a requirement for the drug targeting. Moreover, the lipid-drug conjugates may or may not include a spacer and it is explicitly stated that the conjugates may be pharmacologically active themselves. Though phospholipids included in a list of potentially useful polar lipids, the drug-phospholipid conjugates were clearly never reduced to practice and have not been suggested to be inactive derivatives of the drug.

Mono- and di-esters of methotrexate having short alkyl chains ranging from one to four carbons in length, and MTX mono-esters having alkyl chains of up to sixteen carbon atoms, and their cytotoxic effects on cultured cells in vitro have been disclosed by Rosowsky et. (J. Med. Chem., 1978, 21: 380–386; J. Med. Chem., 1984, 27: 605–609). However, none of the disclosed compounds is a phospholipid derivative of MTX as in the present invention.

Non-lipid analogues of methotrexate have been previously disclosed (for example by Antonjuk, D. et al., 1984 J. Chem. Soc. Perkin Trans. 1 (9) 1989–2003), however the derivatives are monoamides and not phospholipids as in the present invention.

International Application WO 94/22483 describes prodrugs which selectively release pharmacologically active compounds in hyperactivated cells, but does not disclose methotrexate or 5-fluorodeoxyuridine derivatives.

SUMMARY OF THE INVENTION

The object of the present invention is to provide agents with improved anti-proliferative properties. It is a further object of the present invention to provide prodrugs of anti-proliferative drugs that undergo preferential activation within the disease-affected cells and tissues.

The prodrugs in accordance with the present invention comprise a phospholipid moiety covalently linked, via a bridging group, to an anti-proliferative drug residue, such that the active species is preferentially released, preferably by enzymatic cleavage, at the required site of action.

Thus, the present invention provides, in a first aspect, a prodrug of the general formula I:

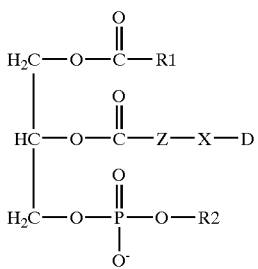

Formula I or a pharmaceutically acceptable salt thereof, wherein:
R1 is a saturated or unsaturated, straight-chain or branched, substituted or unsubstituted hydrocarbon chain having from 2 to 30 carbon atoms;
R2 is H or a phospholipid head group;
Z is saturated or unsaturated, straight-chain or branched, substituted or unsubstituted hydrocarbon chain having from 2 to 15 carbon atoms, which may include cyclic elements, and optionally is interrupted by one or more atoms selected from oxygen and sulfur atoms;
X is a direct covalent bond or selected from the group consisting of O, S, NH and C(O) groups; and
D is a residue of an anti-proliferative drug,
wherein the bound anti-proliferative drug residue is an inactive form of the drug which is selectively activated in cells and tissues with elevated phospholipase activity.

According to a currently preferred embodiment, R1 of the prodrug of the general formula I is a hydrocarbon chain having from 5 to 20 carbon atoms, more preferably 15 or 17 carbon atoms.

In another preferred embodiment R2 of the prodrug of the general formula I is selected from the group consisting of choline, ethanolamine, inositol and serine. Preferred anti-proliferative drugs used in the prodrug of the general formula I are methotrexate and 2'-deoxy-5-fluorouridine.

Currently more preferred prodrugs according to the invention are selected from the group consisting of:
1-Stearoyl-2-[3-(α-MTX amido)-Propanoyl]-sn-Glycero-3-phosphocholine,
1-Stearoyl-2-[3-(γ-dodecylate-α-MTX amido)-Propanoyl]-sn-Glycero-3-phosphocholine,
1-Stearoyl-2-[4-(α-MTX amido)-Butanoyl]-sn-Glycero-3-phosphocholine,
1-Stearoyl-2-[6-(α-MTX amido)-Hexanoyl]-sn-Glycero-3- phosphocholine,
1-Stearoyl-2-[8-(α-MTX amido)-Octanoyl]-sn-Glycero-3- phosphocholine,
1-Stearoyl-2-[8-(γ-dodecylate-α-MTX amido)-Octanoyl]-sn-Glycero-3-phosphocholine,
1-Stearoyl-2-[3-(α-dodecylate-γ-MTX amido)-Propanoyl]-sn-Glycero-3-phosphocholine, and
1-stearoyl-2-[5'''-(2''-deoxy-5'-fluorouridine-5''-)-3''',3'''-dimethyl]glutaroyl-1'''-sn-glycero-3-phosphocholine.

Currently most preferred prodrugs are:

1-Stearoyl-2-[3-((α-MTX amido)-Propanoyl]-sn-Glycero-3-phosphocholine, and 1-Stearoyl-2-[3-(α-dodecylate-γ-MTX amido)-Propanoyl]-sn-Glycero-3-phosphocholine.

In another aspect of the invention, there is provided a pharmaceutical composition comprising a pharmaceutically acceptable carrier and, as an active ingredient, a prodrug of the general formula I as defined above. The pharmaceutical composition, in accordance with the invention, may further include one or more additional anti-neoplastic agents.

In a further aspect, the present invention provides the use of a prodrug of the aforementioned formula I, or a pharmaceutically acceptable salt thereof, for the preparation of a pharmaceutical composition.

In still a further aspect, the invention provides methods for treatment of diseases or disorders related to an inflammatory condition such as granulomatous diseases, arthritis, rheumatoid arthritis, multiple sclerosis, systemic sclerosis, asthma, psoriasis, systemic lupus erythematosus, inflammatory bowel syndromes and migraines. Also provided are methods for treatment of diseases and disorders related to a degenerative or atrophic condition, in particular central or peripheral neurological diseases or disorders. The diseases and disorders related to a degenerative or atrophic condition may be selected from, but are not limited to, the group consisting of autoimmune, cerebrovascular and neurodegenerative diseases and disorders such as idiopathic dementia, vascular dementia, multi-infarct dementia, traumatic dementia, Alzheimer's disease, Pick's disease, Huntington's disease, dementia paralitica, Parkinson's disease, diabetic neuropathy, amyotrophic lateral sclerosis, ischemia of the optic nerve, age-related macular degeneration, stroke and trauma. Also provided are methods for treatment of diseases or disorders related to uncontrolled cell growth. Said diseases or disorders may be selected from, but are not limited to, psoriasis, lymphocytic leukemia, myelogenous leukemia, Burkitt's lymphoma, non-Hodgkin's lymphomas, mycosis fungoides, osteosarcoma, hydatidiform mole, trophoblastic diseases such as chorioadenoma destruens and choriocarcinoma, and carcinomas of the head and neck, breast, liver, lung, colon, ovary, cervix, urinary, bladder, prostate, pancreas, skin, the gastrointestinal tract and the oropharyngeal areas.

The aforementioned methods comprise administering to a patient in need thereof a pharmaceutical composition containing a therapeutically effective amount of a prodrug of the general formula I, in accordance with the invention.

In a preferred embodiment, the prodrugs of the invention are useful for the treatment of neoplastic growths. The neoplastic growths may be primary or secondary tumors, including drug-resistant tumor, for example tumors resistant to methotrexate and multidrug-resistant tumors.

DETAILED DESCRIPTION OF THE INVENTION

Figure 1:
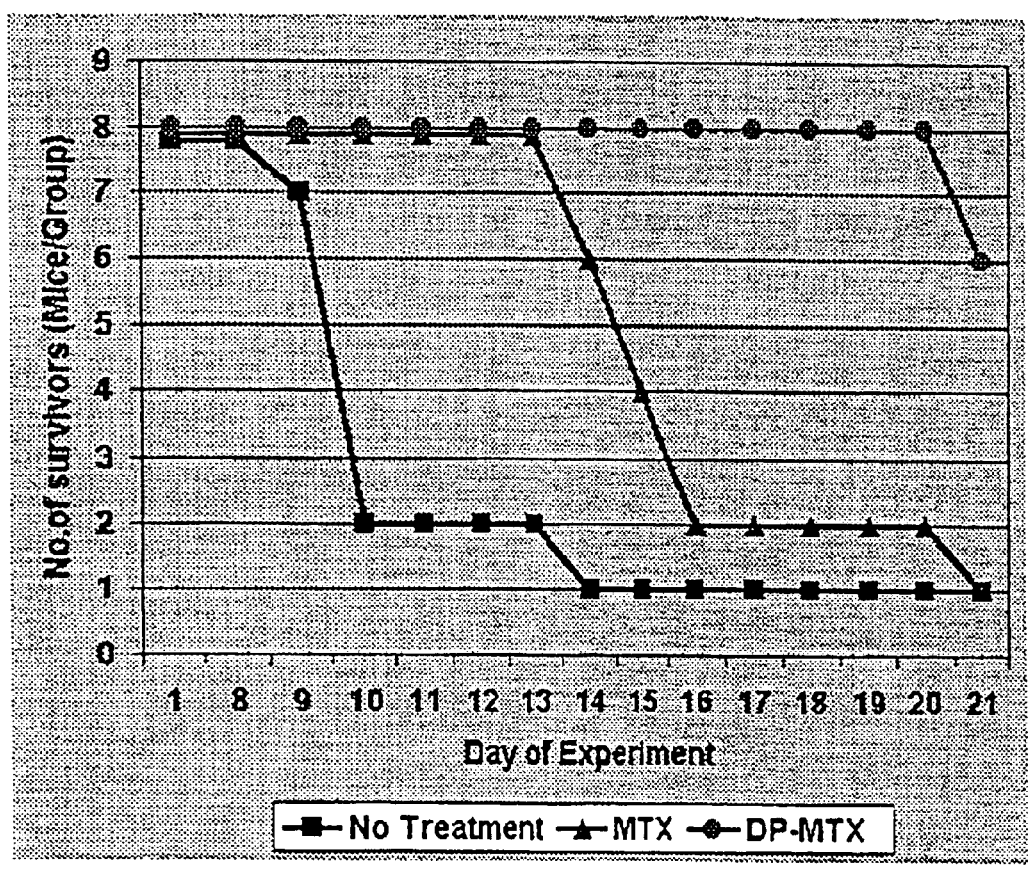
FIG. 1 depicts a graph of animal survival during the course of an experiment wherein mice were i.p. transplanted with L1210 mouse leukemia cells and then treated with vehicle only (squares), MTX (triangles) or molar equivalent dose of DP-MTX-71 (circles) according to the regimen described in Example 11.

The prodrugs of the general formula I according to the present invention comprise anti-proliferative agents covalently conjugated, via a bridging group, to position sn-2 of a phospholipid. These compounds, being hydrophobic in nature, may penetrate biological membranes, thus effectively transporting the prodrug into cells or organs.

According to the principles of the invention, the bound anti-proliferative drug residue is an inactive form of the drug and is linked to the phospholipid moiety through a bridging group that is susceptible to cleavage. The cleavage enables release of an active anti-proliferative drug from the prodrug compound, preferably at the required site of action. The specificity of the drug activation is afforded by a lining group that is designed to be sensitive to cleavage by lipases, preferably phospholipases (e.g. $PLA_2$) that are specifically elevated at the pathological target tissue. According to this process, denoted as Regulated Activation of Prodrugs (RAP), regulated release of the active drug preferentially occurs at the disease site. It should be appreciated that the release of the active anti-proliferative drug from the prodrug may be enzymatically or non-enzymatically executed. Moreover, the released active drug may be different from the original parent drug molecule, including drug derivatives wherein one or more chemical group has been removed from or added to the original anti-proliferative residue D. These cases are also included within the concept of the invention provided that the released drug derivative preserves therapeutic activity. Preferably the cleavage process of the molecule of the invention is initiated specifically at the diseased cells, thus generating a highly specific and highly effective drug release at the desired target site. However, it may not be excluded that under certain pathological conditions, the prodrug molecule may be therapeutically active while the anti-proliferative agent is not cleaved from the phospholipid moiety.

Irrespective of the exact composition of the active component and without wishing to be limited to a particular mechanism of action, it is evident that the novel prodrugs of the invention have an improved therapeutic profile. They also may enable extending the usefulness of anti-proliferative agents to conditions that do not respond to equivalent doses of the parent drug, or permit use of the drugs in certain conditions and diseases where the toxicity of the parent molecule is prohibitive.

While screening the compounds of the invention for their cytotoxic effect on various tumor cell lines, it was unexpectedly found that a currently most preferred compound according to the principles of the invention, denoted herein as DP-MTX-71 showed a remarkable anti-proliferative effect on drug-resistant cells. Thus it was established that certain compounds of the invention may be useful as anti-cancer agents, inhibiting the growth of sensitive as well as resistant tumor cell lines.

In accordance with the principles of the present invention, the various prodrug molecules may be specifically tailored to suit specific target sites and specific indications. In designing a prodrug compound in accordance with the invention, the specific nature of the pathological condition to be treated should be considered. This involves determining the desired pharmacological activity to be achieved, hence the choice of the anti-proliferative drug residue D. In addition, the phospholipid moiety may be modified in order to optimize lipophilicity of the prodrug and drug release.

The desired lipophilicity of the molecule depends on the particular site where the pharmaceutical activity is needed. Accordingly, the number of carbon atoms in the R1 hydrocarbon chain of a prodrug of the general formula I, is determined. The lipophilicity of the molecule is directly correlated to the selected hydrocarbon chain length. R1 chains according to the invention may contain 2 to 30 carbon atoms. Molecules with R1 having from 5 to 20 carbon atoms are most desirable as endowing the molecule with suitable hydrophobicity for crossing biological membranes and at the same time providing adequate substrate for the action of phospholipase. R1 may be a straight-chained or branched, saturated or unsaturated hydrocarbon chain, containing one or more double and/or triple bonds. One or more hydrogen atoms on the chain may be substituted, for example, by halogen atoms or by a small alkyl group such as methyl residues, with the proviso that the substituents still allow free access for the desired cleaving enzymes. In preferred embodiments of the invention R1 is an alkyl residue of an odd number of carbon atoms. More preferably R1 is an alkyl residue of 15 or 17 carbon atoms yielding, respectively, the naturally occurring palmitoyl ($C_{16}$) or stearoyl ($C_{18}$) residues at the sn-1 position of the phospholipid.

The lipophilicity of the lipid molecule is also affected by the nature of the phospholipid head group, denoted as R2 in the prodrug of the general formula I. The phospholipid moiety may be selected from, but is not limited to, the group consisting of phosphatidic acid, phosphocholine, phosphatidylethanolamine, phosphatidylinositol and phosphatidylserine.

The anti-proliferative drug residue incorporated into the phospholipid prodrug may be any anti-proliferative agent that inhibits, directly or indirectly, cell growth. The drug is covalently linked, via a bridging group, to position sn-2 of the phospholipid, such that the anti-proliferative activity of the bound drug residue is significantly reduced.

In one particular embodiment, prodrugs of the invention are phospholipid derivatives of methotrexate. In a preferred embodiment, binding of the drug to the lipid-bridge moiety is specifically directed to the α-carboxylic group of methotrexate (herein denoted α-MTX). It was found that binding of phospholipid to methotrexate via its alpha carboxylic group yields a pharmaceutically inactive methotrexate. In another preferred embodiment, the methotrexate moiety is linked to the phospholipid through the γ-carboxyl of methotrexate (herein denoted γ-MTX).

The hydrogen atom of the carboxylic group of methotrexate that is not attached to the phospholipid, i.e. the γ-carboxylic group of α-MTX or the α-carboxylic group of γ-MTX, may be substituted by a saturated or unsaturated, substituted or unsubstituted hydrocarbon chain having from 2 to 30 carbon atoms.

Preferably, the appropriate drugs are linked to the bridging group through a carboxyl, oxy, amine or mercapto group, thus generating an ester, amido or a thio bond.

Suitable anti-proliferative drugs may include, but are not limited to, anti-metabolites such as paclitaxel, estramustine, melphalan, carmustine, nimustine, daunorubicin, doxorubicin, denopterin, methotrexate, trimetrexate, fluorouracil fluorodeoxyuridine, 6-azauridine, flutamide, nilutamide, goserelin, leuprolide and anthralin.

In currently preferred embodiments of the invention the anti-proliferative drug is selected from methotrexate and 2'-deoxy-5-fluorouridine and pharmaceutically acceptable derivatives thereof.

The anti-proliferative drug residue, D, is covalently linked to the phospholipid moiety via the bridging group —C(O)—Z—X. The choice of the preferred bridging group is dependent on several considerations; it should participate in a stable covalent bond with the D moiety while lending itself to cleavage at the target site. A preferred bridging group, is such that is resistant to cleavage under normal physiological conditions encountered by the administered compound on its way to the target site. The bridging group should not confer a steric hindrance on the enzymatic cleavage of the ester bond at position sn-2 of the phospholipid of the general formula I.

Depending on the treated pathological condition and the particular diseased cell or organ, it will be desirable at times to choose such a bridging group that will regulate the release of the active drug by facilitating or delaying its cleavage from the prodrug molecule.

Component Z of the bridging group may be a saturated or unsaturated, straight-chain or branched hydrocarbon chain having from 2 to 15 carbon atoms, which may include cyclic elements, and optionally is interrupted by one or more atoms selected from oxygen and sulfur atoms. Component X may be a covalent bond or is selected from the group consisting of O, S, NH and C(O) groups. According to a preferred embodiment, the total number of carbon atoms in the bridging group C(O)—Z—X is at least 4 but at most 15. It was found that this length of carbon chain provides a spacer which enables good access to an enzyme, preferably phospholipase and in particular $PLA_2$, for digesting the ester bond at position sn-2 of the phospholipid of the general formula I. Shorter spacers, in particular bridging groups comprising less than three carbon atoms, may be problematic, by creating an unfavorable steric environment for the action of the phospholipase. A situation steric interference may also be generated by long spacers, i.e. when the number of carbon atoms in the bridging chain is greater than 15.

It is important to note that the functional group of D through which the drug residue is bound to the bridging group may be selected from amino, hydroxyl, thiol and carboxyl groups, with the proviso that when the functional group of D is —C(O)OH, X is not a carbonyl, and when the functional group of D is —H, —$NH_2$, —NH or —SH, X is a carbonyl group. The above restrictions are applied since some combinations of X with particular drug residues may be unfavorable as yielding a very labile bond which is spontaneously cleaved, therefore greatly lowering the efficacy of the prodrug. Such an unfavorable combination is, for example, where the covalent bond formed is —(CO)—O—(CO)—. This is a labile bond that tends to dissociate, hence greatly reducing drug bioavailability and therapeutic effects at the target site.

The therapeutic efficacy of any particular compound according to the invention should be evaluated by a person skilled in the art considering the general knowledge in chemotherapy and the teachings of the present invention. The choice of a specific compound to be used as a prodrug according to the invention will also depend on the particular disease or disorder to be treated.

In accordance with another aspect of the invention, there are provided pharmaceutical compositions comprising as an active ingredient a prodrug of the general formula I, together with a pharmaceutically acceptable diluent or carrier as are known in the art.

In particularly preferred embodiments of the invention, there are provided pharmaceutical compositions comprising phospholipid derivatives of methotrexate and fluorodeoxyuridine (herein respectively denoted as DP-MTX and DP-FUdR). Specific derivatives are denoted by numerical suffixes.

The linkage of the anti-proliferative drug moiety to the phospholipid is via a bond that is susceptible to cleavage by phospholipase. Thus, at diseased site characterized by elevated activity of phospholipase, DP-MTX prodrug, for example, is cleaved to release free methotrexate or a therapeutically active derivative thereof The released drug will inhibit dihydrofolate reductase thus depleting intracellular tetrahydrofolate ($FH_4$). DNA synthesis and de novo purine synthesis will, therefore, also be shut down resulting in inhibition of highly proliferative cells, such as cancer cells. Similarly, at the site of inflammation, the specific release of methotrexate leads to inhibition of leukocyte activation and migration, hence suppressing the inflammatory condition. In the case of rheumatoid arthritis, DP-MTX displays improved intra-articular retention in the inflamed synovium and reduced clearance from the joints due to the presence of its hydrophobic phospholipid moiety.

In a similar way DP-FUdRs, the novel phospholipid derivatives of fluorodeoxyuridine, demonstrate improved properties as anti-proliferative prodrugs. The fact that these prodrugs are capable of selectively releasing their pharmaceutically active component at the target site should enable a significant reduction in therapeutic dose coupled with a reduction in the frequency of administration.

The pharmaceutical compositions of the invention are useful in the treatment of diseases and disorders related to inflammatory, degenerative or atrophic conditions and in the treatment of diseases and disorders related to uncontrolled cell growth. The uncontrolled cell growth may include psoriasis and neoplastic growths including, but not limited to, lymphocytic leukemia, myelogenous leukemia, Burkitt's lymphoma, non-Hodgkin's lymphomas, mycosis fungoides, osteosarcoma, hydatidiform mole, trophoblastic diseases such as chorioadenoma destruens and choriocarcinoma, and carcinomas of the head and neck, breast, liver, lung, colon, ovary, cervix, urinary, bladder, prostate, pancreas, skin, the gastrointestinal tract and the oropharyngeal areas.

The pharmaceutical compositions of the invention are applicable in the treatment of neoplastic growths that may be benign or malignant growths including primary tumors as well as secondary tumors such as metastases.

Furthermore, the pharmaceutical compositions of the invention may be useful for the treatment of drug-resistant tumors, e.g. MTX-resistant and multi-drug resistant (MDR) tumors. This aspect of the invention is based on the unexpected findings that one currently most preferred embodiment of the tested compounds, namely DP-MTX-71, was effective in inhibiting cell growth of drug-resistant tumors. Moreover, this prodrug is especially advantageous in that it overcomes MTX-resistance without provoking a MDR phenotype.

In another preferred embodiment, the pharmaceutical compositions are useful for treating diseases and disorders related to an inflammatory condition including, but not limited to, granulomatous diseases, arthritis, rheumatoid arthritis, multiple sclerosis, systemic sclerosis, asthma, psoriasis, systemic lupus erythematosus, inflammatory bowel syndromes and migraines.

In yet another preferred embodiment, the pharmaceutical compositions provided by the invention are useful for treating diseases and disorders related to degenerative or atrophic conditions. Said degenerative or atrophic conditions may include, but are not limited to, autoimmune diseases and cerebrovascular and neurodegenerative diseases or disorders in the central and peripheral nervous system.

It should be appreciated that the prodrugs and pharmaceutical compositions in accordance with the invention may be useful in curative as well as in preventive medical treatments. For example, uncontrolled cell growth, inflammatory and degenerative processes possibly leading to pathological conditions and diseases in the nervous system and blood vessels, may be prevented or inhibited by the prodrugs of the invention. In a particular case, the phenomenon of restenosis, frequently developed following invasive procedures used in the treatment of arteriosclerosis diseases, may be ameliorated or prevented by applying a therapeutically effective amount of an anti-proliferative agent in accordance with the invention. The invasive procedures may include, but are not limited to, vascular surgery procedures such as percutaneous transluminal coronary angioplasty (PTCA) and bypass operations.

The pharmaceutical compositions may include therapeutically effective amounts of a prodrug in accordance with the invention together with one or more additional agents known to be effective in the treatment of a particular disease or disorder. For example, beneficial effects have been observed when methotrexate is used as part of a combination therapy in patients with carcinoma or Burkitt's and other non-Hodgkin's lymphomas. Methotrexate is routinely used in combination with cyclophosphamide and fluorouracil in the treatment of breast cancer, in combination with cisplatin and/or doxorubicin in the treatment of cancer of the bladder, and in combination with cisplatin and bleomycin in the treatment of carcinomas of the cervix and head and neck. In these and other combinations it is possible to substitute one or more of the active drugs for a prodrug according to the invention comprising the corresponding drug residue which may endow the medicament with additional therapeutic value.

The pharmaceutical compositions may be in a liquid, aerosol or solid dosage form, and may be formulated into any suitable formulation including, but not limited to, solutions, suspensions, micelles, emulsions, microemulsions, aerosols, ointments, gels, suppositories, capsules, tablets, and the like, as will be required for the appropriate route of administration.

In yet another aspect, the present invention provides methods for treating pathological conditions related to uncontrolled cell growth, inflammatory and degenerative or atrophic conditions. Said methods comprise administering to an individual in need thereof a therapeutically effective amount of a prodrug of the general formula I or a pharmaceutical composition in accordance with the invention.

The term "therapeutically effective amount" used in the specification refers to the amount of a given prodrug compound according to the invention which antagonizes or inhibits, directly or indirectly, activities associated with inflammatory, degenerative or atrophic processes or uncontrolled cell growth, hence providing either a subjective relief of a symptom(s) or an objectively identifiable improvement as noted by the clinician or other qualified observer.

Any suitable route of administration is encompassed by the invention including, but not being limited to, oral, intravenous, intraperitoneal, intramuscular, subcutaneous, inhalation, intranasal, topical, rectal or other known routes. In preferred embodiments, the pharmaceutical compositions of the invention are orally, intravenously or topically administered.

The dose ranges for administration of the compositions of the invention are those large enough to produce the desired anti-proliferative effect. The dosing range of the prodrug varies with the specific drug used, the treated pathological condition, the route of administration and the potency of the particular prodrug molecule in releasing the drug at the specific target site. The dosage administered will be dependent upon the age, sex, health, weight of the recipient, concurrent treatment, if any, frequency of treatment and the nature of the effect desired. Dosage regimen and means of administration will be determined by the attending physician or other person skilled in the art.

The invention will now be illustrated by the following non-limiting examples, which include detailed description of some specific embodiments of the invention. These examples are illustrative and are not to be read as limiting the scope of the invention as is defined by the claims which follow.

EXAMPLES

CHEMICAL EXAMPLES

Example 1

General Synthesis of Phospholipid Derivatives of Methotrexate (DP-MTX)

A general procedure for the synthesis of DP-MTX compounds is described below. It is important to note that in this protocol a selective binding to the α and γ positions of the methotrexate has been achieved.

Binding between the phospholipid and the MTX in these derivatives is via an ω-aminoacid at position-2 of lipid moiety. The synthesis pathway consists of six steps. Step 1 is protection of an amino group with a benzyloxycarbonyl resulting in the corresponding Z-amino acid. In step 2 the Z-amino acid is converted into the Z amino acid anhydride. Step 3 is synthesis of DP-amino acid, namely the formation of lipid derivative comprising the amino acid with protected amino group and a lyso-lecithin. Step 4 is de-protection, by hydrogenation, of the amino group of the amino acid, In step 5 the mixed anhydride of methotrexate or its γ-esters are prepared by reacting methotrexate (γ-esters) with isobutyl chloroformate in the presence of triethyl amine. In the last stage, step 6, the final product is obtained by reacting the mixed anhydride of methotrexate, or its ester, with 1-acyl-2-(ω-amino) acyl-Sn-glycero-3-phosphocholine in the presence of triethylamine as a catalyst.

For the sake f clarity, each of the intermediary steps will be described below in details.

Stage 1. Protection of the amino group of amino acid (Preparation of Z-amino acid).

To a mixture of 0.1 mol corresponding amino acid (3-aminopropanoic acid, 4-aminobutanoic acid, 6-aminohexanoic acid, 8-aminooctanoic acid etc.) in ethanol (25 ml) in round-bottom flask (250 mol) equipped with a magnetic stirrer and dropped funnel, a solution of NaOH (8.8 g., 0.22 mol) in 100 ml water is added and the mixture is stirred by magnetic stirrer until fully dissolved. The obtained solution is cooled to 0° C. in an ice-water bath, and benzyl chloroformate (27.4 g, 0.15 mol) is added drop wise over 30 min. The reaction mixture is stirred for 3 hours at 0° C. Subsequently, about 100 ml water is added to the reaction solution and the mixture is poured into separated funnel. The water solution is extracted with diethyl ether (3×50 ml). The water phase is separated and acidified with HCl (3N) to pH=1 while cooling in an ice-water bath. If a precipitate is formed, it is filtered, washed with water and dissolved in 100 ml chloroform. The chloroform solution is dried with sodium sulfate for two hours. Then the sodium sulfate is separated from the chloroform solution by filtration and the solvent is evaporated in evaporator under vacuum. The residue is washed with hexane, and dried overnight in vacuum over phosphorus pentoxide ($P_2O_5$).

If a precipitate is not formed, or in order to maximize the product yield, the acidified aqueous fraction is washed with chloroform (2×50 ml). The chloroform extracts are combined and washed with water (50 ml). The following operations with this solution are the same as for the above-described chloroform solution of the precipitate, namely, drying with sodium sulfate for two hours, then separating the sodium sulfate from the chloroform solution by filtration and evaporating the solvent in evaporator under vacuum. The residue is then washed with hexane, and dried overnight in vacuum over phosphorus pentoxide.

All products were analyzed on TLC as follows: TLC analysis. Silica gel 60 on aluminium sheet. Eluent is chloroform-methanol (4:1 v/v). Indicator is a spray of the composition: 4-methoxybenzaldehyde (10 ml), absolute ethanol (200 ml), 98% sulfuric acid (10 ml) and gracial acetic acid (2 ml). The chromatogram is sprayed with the indicator and then charred at 150–180° C.

The following are specific intermediate products obtained at the end of stage 1 of the synthesis procedure:
3-[N-(Benzyloxycarbonyl)amino]propanoic acid. $C_6CH_5$—$CH_2$—O—C(O)—NH—$CH_2$—$CH_2$—COOH.
White solid. Yield 60%. TLC analysis: One spot $R_f$0.7. $^1$H NMR ($CD_3OD$). δ (ppm): 2.46–2.52 (t, 2H, α—$CH_2$ group of alanine), 3.29–3.39 (t, 2H, γ—$CH_2$ group of alanine) 5.06 (s, 2H, benzylic $CH_2$ group), 7.27–7.32 (m, 5H, $C_6H_5$ group).
4[N-(Benzyloxycarbonyl)amino]butanoic acid $C_6H_5CH_2$—O—C(O)—NH—$(CH_2)_3$—COOH.
White solid. Yield 60%. TLC analysis: One spot $R_f$0.7. $^1$H NMR ($CD_3OD$). δ (ppm): 1.71–1.82 (m, 2H), 2.28–2.34 (m, 2H), 3.10–3.17 (t 2H), 5.06 (s, 2H), 7.26–7.34 (m, 5H).
5-[N-(Benzyloxycarbonyl)amino]valeric acid $C_6H_5CH_2$—O—C(O)—NH—$(CH_2)_4$—COOH.
White solid. Yield 60%. TLC analysis: One spot. $R_f$=0.7. $^1$H NMR ($CD_3OD$) δ (ppm): 1.45–1.50 (m 2H), 1.56–1.62 (m, 2H), 2.25–2.31 (t, 2H) 3.08–3.13 (t, 2H), 5.05 (s, 2H), 7.26–7.34 (m, 5H).
6-[N-(Benzyloxycarbonyl)amino]hexanoic acid $C_6H_5CH_2$—O—C(O)—NH—$(CH_2)_2$—COOH.
White solid. Yield 50%. TLC analysis: One spot. $R_f$0.7. $^1$H NMR ($CD_3OD$). δ (ppm): 1.30–1.63 (m, 6H), 2.24–2.30 (t, 2H), 3.07–3.13 (t, 2H), 5.05 (s, 2H), 7.29–7.34 (m, 5H).
8-[N-(Benzyloxycarbonyl)amino]octanoic acid $C_6H_5CH_2$—O—C(O)—NH—$(CH_2)_2$—COOH.
White solid. Yield 50%. TLC analysis: One spot. $R_f$0 7. $^1$H NMR ($CD_3OD$). δ (ppm): 1.32 (bs, 6H), 1.47–1.50 (m, 2H), 1.53–1.59 (m, 2H), 2.23–2.29 (t, 2H), 3.06–3.12 (t, 2H), 5.05 (s, 2H), 7.29–7.34 (m, 5H).

Stage 2. Synthesis of Z-amino acid anhydride.

The solution of the corresponding Z-aminoacid produced at stage 1 (0.05 mol) in freshly distilled dichloromethane (25 ml) is introduced, under an atmosphere of argon, into double-neck round-bottom equipped with magnetic stirrer and dropped funnel. A solution of dicyclohexylcarbodiimide (DCC) (0.0325 mol) in 25 ml of freshly distilled dichloromethane, also under argon, is added drop wise, with stirring, to the solution of Z-amino acid. After 20 min of stirring, the obtained precipitate of urea is filtered and the solution evaporated under vacuum. The crude residue is washed with hexane (2×20 ml) to remove remaining DCC and then dried in vacuum.

TLC analysis: The same procedure is used for TLC analysis of anhydride of the all Z-amino-acids. Silica gel 60 on aluminium sheet Eluent is the mixture of chloroform with methanol (9:1 v/v). For indication, ninhydrine spray is used on the chromatogram followed by charring (100–150° C.). The following are specific intermediate products obtained at the end of stage 2:
Anhydride of Z-(3-amino)propanoic acid White solid. Yield is 70%.
TLC analysis: One spot $R_f$0.8.
Anhydride of Z-(4-amino)butanoic acid White solid. Yield is 70%.
TLC analysis: One spot. $R_f$0.8.
Anhydride of Z-(5-amino) valeric acid White solid. Yield is 70%.
TLC analysis: One spot. $R_f$0.8.
Anhydride of Z-(6-amino)hexanoic acid White solid. Yield is 70%.
TLC analysis: One spot. $R_f$0.8.
Anhydride of Z-(8-amino)octanoic acid White solid Yield is 75%.
TLC analysis: One spot. $R_f$0.85.

Stage 3. Preparation of 1-acyl-2-(Z-amino)acyl-sn-glycero-3-phosphocholine.

The anhydride of the corresponding Z-amino acid, 0.01 mol dissolved in 150 ml of freshly distilled chloroform, is introduced, under an inert atmosphere of argon, into a single-neck round-bottom flask (250 ml) equipped with a magnetic stirrer. To this solution 0.01 mol (1.22 g) 4-(dimethylamino)pyridine (DMAP) in 25 ml chloroform is added, followed by addition of a suspension of 0.0056 moles lyso-lecithin in 50 ml of chloroform. The reaction mixture is vigorously stirred for 3–5 hours at room temperature. The lyso-lecithin dissolves and reaction mixture becomes transparent after about 2 hours of stirring. The reaction is monitored by TLC using silica gel 60 on aluminum sheet, the eluent is chloroform:methanol:water, 65:35:5, the indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator followed by charring at 150° C. The reaction is assumed to be complete and stopped when all the lyso-lecithin has disappeared. The reaction mixture is then transferred into a separating funnel and washed with a solution of 1% HCl (3×50 ml), then with saturated solution of sodium bicarbonate (3×50 ml) and finally with water (3×50 ml). The obtained product in the organic solution is dried over sodium sulfate and then filtered. The solvent is evaporated at 30° C. in vacuo and the residue is washed with hexane and left to dry overnight under vacuum. The resultant molecule 1-acyl-2Z-amino)acyl-sn-glycero-3-phosphocholine is the main product of the reaction. TLC analysis: Silica gel 60 on aluminium sheet. Eluent is chloroform/methanol/water (65:35:5 v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred at 100–150° C. The following are specific intermediate products obtained at the end of stage 3:

1-Stearoyl-2-{3'-[N-(Benzyloxycarbonyl)amino]}propanoyl-sn-glycero-3-phosphocholine, White wax. Yield 70%. TLC analysis: One spot. $R_f 0.55$ 1-Stearoyl-2-{4'-[N-(Benzyloxycarbonyl)amino]}propanoyl-sn-glycero-3-phosphocholine, White wax. Yield 70%. TLC analysis: One spot. $R_f 0.55$.

1-Stearoyl-2-{5'-[N-(Benzyloxycarbonyl)amino]}valeroyl-sn-glycero-3-phosphocholine, White wax. Yield 65%. TLC analysis: One spot. $R_f 0.55$.

1-Stearoyl-2-{6'-[N-(Benzyloxycarbonyl)amino]}hexanoyl-sn-glycero-3-phosphocholine, White wax. Yield 65%. TLC analysis: One spot. $R_f 0.55$.

1-Stearoyl-2-{8'-[N-(Benzyloxycarbonyl)amino]}octanoyl-sn-glycero-3-phosphocholine White wax. Yield 65%. TLC analysis: One spot. $R_f 0.55$.

Stage 4. Reduction of amide group of amino acyl lipid.

The obtained 1-stearoyl-2-{ω-[(N-Benzyloxycarbonyl)amino]}acyl-3-phosphocholine (0.0025 mol) is dissolved in a mixture of 100 ml methanol and 5 ml acetic acid. The solution is introduced into round bottom double neck flask (200 ml) equipped with a magnetic stirrer, under an atmosphere of argon. Pd/C (0.5 g) is added to the solution and hydrogen is blown through the reaction mixture for 4 hours. The reaction proceeding is monitored by TLC analysis under the following conditions: silica gel 60 on aluminium sheet, eluent is the mixture of chloroform/methanol/water (65:35:5 v/v), indicator is a spray of the composition: p-methoxybenzaldehyde (10 ml), absolute ethanol (200 ml), 98% sulfuric acid (10 ml) and glacial acetic acid (2 ml). The chromatogram is sprayed with the indicator and then charred at 100–150° C.

The reaction assumed to be complete and hydrogenation is stopped after the corresponding 1-stearoyl-2-Benzyloxycarbonylaminoacyl-sn-glycero phosphocholine has disappeared from the reaction mixture. The reaction mixture is then filtered through Wattman paper to remove the Pd/C, evaporated at 30° C, under vacuum. The crude residue is washed with ether (3×30 ml) and dried in vacuo overnight.

Conditions of the TLC analysis are the same as indicated above. The following are specific intermediate products obtained at the end of stage 4:

1-Stearoyl-2-(3-amino)propanoyl-sn-glycero-3-phosphocholine, acetic acid.

White wax. Yield 70%. TLC analysis: One spot. $R_f 0.2$.

1-Stearoyl-2-(4-amino)butanoyl-sn-glycero-3-phosphocholine, acetic acid.

White wax. Yield 70%. TLC analysis: One spot. $R_f 0.2$.

1-Stearoyl-2-(5-amino) valeroyl-sn-glycero-3-phosphocholine, acetic acid.

White wax. Yield 65%. TLC analysis: One spot. $R_f 0.2$.

1-Stearoyl-2-(6-amino)hexanoyl-sn-glycero-3-phosphocholine, acetic acid.

White wax. Yield 65%. TLC analysis: One spot. $R_f 0.2$.

1-Stearoyl-2-(8-amino)octanoyl-sn-glycero-3-phosphocholine, acetic acid.

White wax. Yield 65%. TLC analysis: One spot. $R_f 0.2$.

Stage 5. Synthesis of the mixed anhydride of methotrexate Freshly distilled diethylformamide (DMF) (25 ml) and THF (75 ml) is introduced, under atmosphere of argon, into a double-neck round-bottom flask (150 ml), equipped by magnetic stirrer and thermometer. Methotrexate (MTX, 0.454 g., 1 mmol) and triethylamine (0.182 g., 239 μkl, 1.8 mmol) are added, under the same conditions, and dissolved in the solvent with stirring.

In protocols for the synthesis of DP-ester-MTX compounds, the MTX was replaced by a α- or γ-ester derivative of MTX wherein the hydrogen atom of the α or γ carboxylic group of methotrexate is substituted by an alkyl group of from 2 to 30 carbon atoms. The ester derivatives of MTX were prepared according the procedure described by Rosowsky et al. (J. Medicin. Chem., 1978, 21: 380–386). The reaction mixture is then cooled to −25° C. in dry ice-acetone bath. Isobutyl chloroformate (0.166 g., 163 μl, 1.2 mmol) is added dropwise to the reaction mixture over 30 min. During this procedure and the following 30-min, the temperature of the reaction mixture is maintained at −25° C. The obtained product is a white precipitate, which is not extracted from reaction mixture but was directly used in the next stage of the synthesis.

Stage 6. Synthesis of α- or γ-monoamide of methotrexate (DP- α-MTX monoamide and DP-γ- MTX monoamide, respectively)

A solution comprising the corresponding 1-stearoyl-2-ω-aminoacyl-sn-glycero-3-phosphocholine of stage 4, acetic acid (0.589 g., 0.9 mmol) and triethylamine (0.182 g., 239 μl, 1.8 mmol) in 30 ml of dry freshly distilled chloroform is added dropwise to the reaction mixture of stage 5 for 30 min at −25° C. The reaction mixture is stirred for additional one hour at −25° C., and then for overnight at room temperature. The solvents are removed in evaporator under reduced pressure. The obtained residue is a thick viscous liquid. Diethyl ether (50 ml) is added to this liquid and the mixture is stirred. The product is gradually transformed into a yellow powder which is filtered and washed with diethyl ether (3×20 ml). The crude product is purified by column chromatography as follows: 450 g. crude product is dissolved in 50 ml of methanol, followed by addition of 11.0 g. dry silica gel. The mixture is swirled, and then the volatile liquid is evaporated under reduced pressure to yield free-flowing yellow finely divided solid. The obtained solid is packed on top of a silica column (3×30 cm) (100 g. silica gel per 1 g of crude product). The product is eluted in succession with the solution MeOH:H$_2$O of variable composition: first fraction is 100:0 (v/v) (1L), second fraction is 99:1 (v/v) (1L), third fraction is 98:2 (v/v) (1L), and fourth fraction is 98:3 (v/v) (2L). The fractions, which contain the product (the determination is carried out by TLC analysis), are combined and the solvent is evaporated under reduced pressure. The obtained product (about 250 mg) is dissolved in mixture of methanol (10 ml) and chloroform (250 ml). The solution is washed with 1% HCl (3×20 ml) and then with water (3×20 ml). To achieve better separation of the aqueous and organic phases, isopropanol (about 25% of the volume of solution) is added. Isopropanol addition also promotes transition of the product into the organic phase. The organic layers are combined and dried over sodium sulfate. The sodium sulfate is filtered off and the solvent is distilled under reduced pressure. The obtained product is dried under vacuum for 3 hours.

Examples of resulted final products and their analyses are:

1-Stearoyl-2-[3-(α-MTX amido)]-proponoyl-sn-glycero-3-phosphocholine, $C_{49}H_{79}N_{10}O_{12}P$.

Yield 35%. Yellow solid. Decompose at 200° C. without melting. pH 5.1. TLC analysis: Silica gel on aluminium plates. Eluent is $CH_3OH:H_2O$ (98:2, v/v). Indication by UV-Vis spectrum. One spot. $R_f$ 0.16. MS(FAB). $C_{49}H_{79}N_{10}O_{12}P$. Main peak (+FAB) is 1031.2. $^1H$ NMR ($CD_3OD$), δ (ppm): 0.89 (t, 3H), 1.22–1.29 (broad s, 30H), 1.53 (m, 2H), 2.08 (m, 2H), 2.35 (m, 2H), 2.60 (t, 2H), 2.50 (t, 2H), 3.21 (s, 3H), 3.38 (s, 9H), 3.47 (t, 2H), 3.93–4.31 (m, 8H), 4.41 (m, 1H), 4.80 (s, 2H), 5.21 (m, 1H), 6.84 (d, 2H), 7.76 (d, 2H), 8.60 (s, 1H). $^{31}P$ NMR ($CD_3OD$), δ (ppm): –3.3 (s). Chemical analysis: $C_{49}H_{79}N_{10}O_{12}P.HCl.3H_2O$. Calculated: C 52.47%, H 7.55%, N 12.49%, P 2.76%, Cl 3.16%. Found: C 52.92%, H 7.76%, N 12.21%, P 2.46%, Cl 30 3.08%.

1-Stearoyl-2-[6-(α-MTX amido)]-hexanoyl-sn-glycero-3-phosphocholine $C_{25}H_{85}N_{10}O_{12}P$.
Yield 40%. Yellow solid. Decomposes without melting at 200° C. pH 5.0. TLC analysis: Silica gel on aluminium plates. Eluent is $MeOH:H_2O$ (98:2, v/v). Indication is UV-Vis spectra. One spot $R_f$ 0.18. MS (FAB): $C_{52}H_{85}N_{10}O_{12}P$ 1073.3 (+FAB) is main peak. $^1H$ NMR ($CD_3OD$), δ (ppm): 0.86–0.89 (t, 3H), 1.22–1.30 (broad s, 32H), 1.51–1.55 (m, 4H), 2.06–2.10 (m, 4H), 2.33–2.36(m, 2H), 2.58–2.62 (t, 2H), 2.49–2.52 (t, 2H), 3.22 (s, 3H), 3.38 (s, 9H), 3.45–3.48 (t, 2H), 3.92–4.35 (several m, 8H), 4.40–4.42 (m, 1H), 4.79 (s, 2H), 5.20 (n, 1H), 6.82–6.84 (d, 2H), 7.74–7.76 (d, 2H0, 8.58 (s, 1H). $^{31}P$ NMR ($CD_3OD$), δ (ppm): –3.7 (s). Chemical analysis: $C_{52}H_{85}N_{10}O_{12}P.2HCl.5H_2O$: Calculated: C 50.48%, H 7.84%, N 11.33%/, P 2.51%, Cl 5.74%. Found: C 50.45%, H 7.220/a, N 11.46%, P 2.43%, Cl 5.43%.

1-Stearoyl-2-[3-(α-dodecylate-γ-MTX amido)]-proponoyl-sn-glycero-3-phosphocholine. $C_{61}H_{103}N_{10}O_{12}P$.
Yield 40%. Yellow solid. Decompose at 200° C. without melting. TLC analysis: Silica gel on aluminium plates. Eluent is $CHCl_3:CH_3OH:H_2O$ (65:35:5, v/v). Indication by UV-Vis spectrum. One spot. $R_f$ 0.17. MS(FAB). $C_{61}H_{103}N_{10}O_{12}P$. Main peak (+FAB) is 1198.4. $^1H$ NMR ($CD_3OD+CDCL_3$), δ (ppm): 0.82–0.85 (t, 3H), 1.23 (broad s, 46H), 1.53–1.58 (m, 2H), 2.24–2.34 (m, 3H), 2.50–2.52 (m, H), 3.17 (s, 9H), 3.41 (t, 1H) 3.54 (s, 1H), 4.04–4.18 (m, 4H), 4.32–4.47 (m, 1H), 4.80 (s, 2H), 5.21 (m, 1H), 6.79–6.82 (d, 2H), 7.76 (d, 2H), 8.54 (s, 1H). $^{31}P$ NMR ($CD_3OD+CDCL_3$), δ (ppm): +0.71 (s). Chemical analysis: $C_{61}H103N_{10}O_{12}P.3H_2O$. Calculated: C 58.47%, H 8.71%, N 11.18%, P 2.47%. Found: C 58.67%, H 8.88%, N 11. 15%, P 2.47%.

Example 2

General Synthesis of Phospholipid Ester Derivatives of Methotrexate (DP-MTX Esters)

The synthetic procedure for the preparation of DP-MTX-esters is a three-stage process.

Stage 1. Synthesis of ω-bromoalkylcarboxylic anhydride.

The solution of the corresponding (ω-bromoalkyl acid (0.05 mol) in freshly distilled dichloromethane (25 ml) is introduced, under an inert atmosphere of argon, into double-neck round-bottom equipped with magnetic stirrer and dropping funnel. A solution of dicyclohexylcarbodiimide (DCC) (0.0325 mol) in 25 ml freshly distilled dichloromethane, also under argon, is added drop wise, with stirring, to the solution of Z-amino acid. After 20 min of stirring, the produced urea precipitate is filtered and the obtained solution is evaporated under vacuum. The crude residue is washed with hexane (2×20 ml) to remove remaining DCC and then dried in vacuum.

Stage 2. Preparation of 1-acyl-2-ω-bromoalkylcarboxy-sn-glycero3-phosphocholine.

0.01 mol of the corresponding ω-bromoalkyl-carboxylic anhydride (obtained in stage 1) dissolved in 150 ml freshly distilled chloroform, is introduced, under an inert atmosphere of argon, into a single-neck round-bottom flask (250 ml) equipped with a magnetic stirrer. To this solution 0.01 mol (1.22 g) 4-(dimethylamino)pyridine (DMAP) in 25 ml chloroform is added, followed by addition of a suspension of 0.0056 moles lyso-lecithin in 50 ml chloroform. The reaction mixture is vigorously stirred for 3–5 hours at room temperature. The lyso-lecithin dissolves and reaction mixture becomes transparent after about 2 hours of stirring. The reaction is monitored by TLC using silica gel 60 on aluminium sheet, the eluent is chloroform:methanol:water, 65:35:5, the indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator followed by charring with hot air at 150° C. The reaction is assumed to be complete and is stopped when all the lyso-lecithin has disappeared. The reaction mixture is then transferred into a separating funnel and washed with a solution of 1% HCl (3×50 ml), then with saturated solution of sodium bicarbonate (3×50 ml) and finally with water (3×50 ml). The organic phase is dried over sodium sulfate and then filtered. The solvent is evaporated at 30° C. in vacuo and the obtained residue is washed with hexane and left to dry overnight under vacuum. The desired molecule 1-acyl-2-ω-bromoalkylcarboxy-sn-glycero-3-phosphocholine is the main product of the reaction.

Stage 3. Synthesis of α-monoesters of methotrexate (DP-α-MTX esters)

A solution of 1-Stearoyl-2-ω-bromoalkylcarboxy-sn-glycero-3-phosphocholine (0.016 mole) in 50 ml dimethyl sulfoxide (DMSO) (freshly distilled over $CaH_2$) is added to a mixture of methotrexate free acid (0.008 mole) and $CsCO_3$ (0.008 mole) in DMSO (150 ml) under an atmosphere of argon. The reaction mixture is stirred at room temperature for 48 hours. The solvent is evaporated under vacuum (1–2 mm Hg, 50° C.). The obtained residue is acidified with 1% HCl to pH=3, followed by an overnight incubation at 0° C. The mixture is then filtered, washed with water and dried over $P_2O_5$ under vacuum. The resultant product is 1-stearoyl-2-[ω-(α-MTX) alkyl]-oxycarbonyl-sn-glycero-3-phosphocholine. This crude product is purified by column chromatography (I g. crude product per 100 g. Silica gel 60) using the eluent: $CHCl_3$: MeOH: $H_2O$ (v/v 40:9:1)

Example 3

Synthesis of Phospholipid Derivatives of 2'-deoxy-5-fluorouridine (DP-5FUdR)

The procedure for the synthesis of DP-5FUdR compounds of the invention is exemplified below by the synthesis of the specific compound 1-stearoyl-2-[5'''-(2''-deoxy-5'-fluorouridine-5''-)-3''',3'''-dimethyl]glutaroyl-1'''-sn-glycero-3-phosphocholine. The detailed description of the synthesis is described below. The products of the different stages of the synthesis are denoted as compounds (1) to (5).

Stage 1. Preparation of 5'-O-Trityl 5-fluoro-2'-deoxyuridine (1).

5-Fluoro-2'-deoxyuridine (2 g, 8.8 mmol) was dissolved in 40 ml dry pyridine under 30 an atmosphere of nitrogen. Trityl chloride (3.6 g, 12.6 mmol) was added and the reaction mixture stirred at room temperature for 48 hours.

The reaction was quenched with methanol (20 ml), and then the mixture was concentrated to dryness under reduced pressure. The compound was purified on silica gel (flash), using chloroform/methanol (97/3) as an eluent. 4.1 g of the product (1) was obtained as a colorless, crystalline solid. Yield—990%.

Stage 2. Preparation of 3'-O-Levulinoyl 5-fluoro-2'-deoxyuridine (2).

The mixture of levulinic acid (2.32 g, 20 mmol), N,N'-dicyclohexylcarbodiimide (2.06 g, 10 mmol) and ether (60 ml) was stirred at room temperature for 5 hours, followed by filtration and evaporation of the solvent. The obtained compound was dissolved in anhydrous pyridine (10 ml). To the solution, compound (1) (4 g, 8.5 mmol) was added. The mixture was stirred for 24 hours at room temperature. Then~50 g chipped ice was added and the reaction mixture was stirred until all the ice melted. The reaction mixture was extracted with chloroform (4×20 ml), and the combined extracts were dried over anhydrous $MgSO_4$. Concentration under reduced pressure followed by removal of excess pyridine under high vacuum yielded 3'-levulinoyl-5'-trityl-5-fluoro-2'-deoxyuridine as yellow oil. This product was re-dissolved in 80% acetic acid (20 ml) and heated for 20 min at 100° C. The reaction mixture was then evaporated under reduced pressure, followed by repeated evaporation from benzene in order to remove traces of water and acetic acid. The resultant reaction mixture was then purified by flash chromatography on silica gel, using chloroform/methanol (40/1). 1.3 g of compound (2) was obtained as white powdery solid. Yield—46%.

Stage 3. Preparation of 1-Stearoyl-2-3",3"-dimethyl-glutaroyl-sn-glycero-3-phosphocholine (3).

A solution of 1-stearoyl-sn-glycero-3-phosphocholine (1.8 g, 3.6 mmol), 3,3-dimethylglutaric anhydride (3.5 g, 25.2 mmol), sodium salt of 2-propylpentanoic acid (0.5 g, 3.2 mmol) in N,N-dimethylformamide (20 ml) was heated for 5 hours at 90° C. The reaction mixture was concentrated to dryness under high vacuum. The residue was dissolved in chloroform/methanol (2/1) 100 ml and washed with 0.1 N HCl (2×50 ml). After evaporation and flash chromatography on silica gel ($CHCl_3$/MeOH/$H_2O$/AcOH 60/30/4/1), 2 g of compound (3) was obtained as white crystalline solid, Yield—87%.

Stage 4. Preparation of 1-Stearoyl-2-[5"-O-(-3'-O-levulinyl-5-fluoro-2'-deoxyuridine)-3",3"-dimethylglutaroyl]-sn-glycero-3-phosphocholine (4).

To 1 g of compound (3) (1.5 mmol), 2.0 M solution of oxalyl chloride in dichloromethane (20 ml, 4 mmol) was added. The mixture was stirred overnight at 20° C. The acid chloride was separated from the oxalyl chloride by removal of the volatiles in vacuum followed by two cycles of dissolution in dry benzene (20 ml) and evaporation.

A solution consisting of compound (2) (700 mg, 2.15 mmol) and triethylamine (0.22 g, 2.17 mmol) in dichloromethane (10 ml) was added drop wise to solution of the acid chloride in dichloromethane (10 ml) at 0° C. The mixture was left overnight at 20° C., then the volatile solvents were removed and the residue was dissolved in chloroform/methanol (2/1, 50 ml) and washed with 0.1N HCl (20 ml). The solvent was removed and the residue was subjected to chromatography on silica gel using methanol/chloroform (10–33%) followed by water/methanol/chloroform (2/30/60) to yield 700 mg of compound (4). Yield—48%.

Stage 5. Preparation of 1-stearoyl-2-[5'''-(2"-deoxy-5'-fluorouridine5"-)-3''',3'''-dimethyl]glutaroyl-1'''-sn -glycero-3-phosphocholine(5).

Hydrazine monohydrate (0.25 ml, 4.8 mmol) in pyridine/acetic acid (3:2 v/v; 5 ml) was added to compound (4) (200 mg, 0.2 mmol) dissolved in pyridine (5 ml). After 2 min at 20° C., the solution was cooled to 0° C. and 2-pentanone (2 ml) was added. The reaction mixture was then evaporated to dryness. Preparative TLC using water/methanol/chloroform (5/35/60) as the solvent yielded 120 mg of the final product (5). Yield—68%.

II. BIOLOGICAL EXAMPLES

Example 4

Evaluation of Anti-proliferative Activity of Methotrexate Derivatives (In Vitro Study)

A series of methotrexate derivatives were screened for their inhibitory effect on cell growth. Three tumor cell lines were used for this screen: i) human leukemia cell line CCRF-CEM which is MTX-sensitive (herein denoted as CEM), ii) a mutant of CEM cell line which is MTX-resistant due to a mutation in the RFC (herein denoted as CEM-MTX; provided by Dr. Y. Assraf, Technion, Israel), and iii) rat C6 glioma cell line.

Cells were seeded at a density of $10^4$ cells/ml in RPMI medium supplemented with 10% FCS in 96 well plates. The cultured cells were incubated, during their linear growth phase, in the presence and absence of various concentrations of MTX derivatives. The tested compounds were prepared as 1 mM stock in absolute ethanol or DMSO and were diluted into the medium. The highest vehicle presence in the assay was 5% of the vehicle. After 72 hours at 37° C. the cytotoxic effect on the cells was estimated by using the colorimetric MTT assay (Mosmann (1983) J. Immunol Methods 65: 55–63) that measures mitochondrial reductase activity and serves for quantitative assessment of cellular viability. Drug concentration required for inhibiting the growth of 50% of cell population in culture over a 72 hour period incubation, is defined as $EC_{50}$.

The $EC_{50}$ values were calculated from dose response curves for each tested compound. The results of this screen are presented in Table 1.

The following MTX derivatives were tested:

α:-dodecylate-MTX (MTX47);

γ-dodecylate-MTX (MTX48);

α-dodecylate-MTX-γ-dodecylate (MTX-256);

1-Stearoyl-2-[3-(α-dodecylate-γ-MTX amido)-Propanoyl]-sn-Glycero- 3-phosphocholine (denoted DP-MTX-71);

1-Stearoyl-2-[3-(α-MTX amido)-Propanoyl]-sn-Glycero-3-phosphocholine (denoted DP-MTX-93);

1-Stearoyl-2-[4-(α-MTX amido)-Butanoyl]-sn-Glycero-3-phosphocholine (denoted DP-MTX-129);

1-Stearoyl-2-[6-(α-MTX amido)-Hexanoyl]-sn-Glycero-3-phosphocholine (denoted DP-MTX-106);

1-Stearoyl-2-[8-(α-MTX amido)-Octanoyl]-sn-Glycero-3-phosphocholine (denoted DP-MTX-142);

1-Stearoyl-2-[3-(γ-dodecylate-α-MTX amido)Propanoyl]-sn-Glycero-3-phosphocholine (denoted DP-MTX-128); and 1-Stearoyl-2-[8-(γ- dodecylate-α-MTX amido)-Octanoyl]-sn-Glycero-3-phosphocholine (denoted DP-MTX-127).

The cytotoxic activity of the DP-MTX derivatives on the tested cells was compared to that of commercial MTX (Abitrexate®, from ABIC, Israel; or Sigma cat. # M 8407).

TABLE 1

Effect of various derivatives of MTX on cell growth

| Compound | $EC_{50}$, nMol CEM | $EC_{50}$, nMol CEM-MTX | $EC_{50}$, nMol C6 glioma |
|---|---|---|---|
| MTX | 21 | 2535 | 46 |
| α-$C_{12}H_{25}$-MTX | 88 | 9423 | |
| γ-$C_{12}H_{25}$-MTX | 13 | 4864 | |
| α-$C_{12}H_{25}$-MTX-γ-$C_{12}H_{25}$ | 4855 | 5093 | 807 |
| DP-MTX-71 | 169 | 213 | 14 |
| DP-MTX-93 | 27 | 4651 | 417 |
| DP-MTX-129 | 821 | 5982 | 3109 |
| DP-MTX-106 | 499 | 8398 | 3219 |
| DP-MTX-142 | 6344 | 11591 | 35982 |
| DP-MTX-128 | 771 | 1602 | |
| DP-MTX-127 | | | 795 |

As can be seen from the results in Table 1, the various tested DP-MTX derivatives were active to a different degree in their ability to inhibit cell growth of the human leukemia cell lines and the rat glioma cells. Among the tested DP-MTX derivatives, the most effective in inhibiting CEM cell growth was DP-MTX-93, having $EC_{50}$ value which is similar to that of the parent drug MTX. Another compound, DP-MTX-71, was found to exhibit a significantly improved effect in inhibiting cell growth of the resistant cell line CEM-MTX. The DP-MTX-71 derivative of MTX was about 10 fold more active in its cell growth inhibition effect on the resistant cell line in comparison to the parent drug, MTX.

DP-MTX-71 has demonstrated similar $EC_{50}$ values for both the leukemia cell line CEM and the mutant MTX-resistant cell line, CEM-MTX and was found to be especially effective in inhibiting growth of the C6 glioma cell line. It is important to note that α—$C_{12}H_{25}$-MTX, γ—$C_{12}H_{25}$-MTX and the di-ester α—$C_{12}H_{25}$-MTX-γ—$C_{12}H_{25}$ were not effective in inhibiting the growth of the MTX-resistant cell line, CEM-MTX.

Conclusion: DP-MTX-93 and DP-MTX-71 were identified as the most efficacious of the tested MTX-derivative compounds. The DP-MTX-71 compound that, unexpectedly, was found to be active also in inhibiting the MTX-resistant tumor cell line, was chosen to be used in further experiments aimed to analyze in more detail the cytotoxic effect of DP-MTX.

Example 5

Evaluation of Cytotoxicity of Methotrexate Derivatives (In Vitro)

The toxicity of methotrexate derivatives of the invention (DP-MTX) was evaluated in an additional cell-culture system. The doses required to inhibit the growth of cultured Friend cells (an erythroleukemic cell line) by 50%, over a 72 hour period ($ED_{50}$), were determined using a mitochondrial viability (MTT) endpoint assay.

Friend cells were seeded at a density of $10^4$ cells/ml in RPMI medium supplemented with 10% FCS in 96 well plates. The cultured cells were incubated, during their linear growth phase, in the presence and absence of various concentrations of MTX derivatives. After 72 hours at 37° C., cell viability was estimated by using the colorimetric MTT assay.

TABLE 2

| Compound | n | R | $ED_{50}$, nMol |
|---|---|---|---|
| MTX (control) | — | — | 10 |
| α-MTX | | | |
| DP-MTX-93 | 2 | H | 97.5 |
| DP-MTX-129 | 3 | H | 97.5 |
| DP-MTX-106 | 5 | H | 390 |
| DP-MTX-142 | 7 | H | 3000 |
| γ-MTX | | | |
| DP-MTX-71 | 2 | $C_{12}H_{25}$ | 23 | n is the number of carbon atoms in the linker between the MTX residue and the phospholipid moiety; R is the substituent at the γ- or α-carboxylic group of the α-MTX and γ-MTX compounds, respectively.

Of the tested MTX derivatives, DP-MTX-93, DP-MTX-129, DP-MTX-106 and DP-MTX-142 are α-MTX derivatives, namely molecules wherein MTX is linked to the lipid moiety through its α-carboxylic croup. MTX-71, on the other hand, is a γ-MTX derivative, namely a molecule wherein MTX is linked through its γ-carboxyl instead of its cl-carboxylic group. In addition, MTX-71 has an R residue, $C_{12}H_{25}$ group, linked to its α-carboxyl.

As can be seen in Table 2, DP-MTX-71 was about 2-fold less active than the parent drug MTX in inhibiting Friend cells' growth. DP-MTX-71 was 4-fold more active compared to the α-MTX derivative, DP-MTX-93, which has the same bridging group.

Overall, under the conditions of the experimental system used, all tested DP-MTX derivatives, and especially DP-NM-142, were less cytotoxic than the parent drug MTX (control). The tested alpha-DP-MTX derivatives were about 10- to 300-fold less toxic than MTX. These results indicate that alpha-DP-MTX derivatives are inactive prodrugs of the active species MTX.

Example 6

Effect of DP-MTX on DHFR Activity in order to further explore the cytotoxic effect of DP-MTX-71, the activity of this compound was measured on cell cultures of the human tumor cell CEM in the presence or absence of Leucovorin. Leucovorin is a reduced folate, used in chemotherapy with high doses of methotrexate for 'rescue' of host from toxicity.

Wild type human leukemia CEM cells or the MTX-resistant mutant cells, CEM-MTX, were plated into 96 well plates containing RPMI, 10% FCS at a concentration of $5 \times 10^4$ cells/ml. Either commercial MTX or the MTX derivative DP-MTX-71 was added at decreasing concentrations. Leucovorin, at a final concentration of 10 μM, was added to some of the plates as indicated. The plates were incubated for 72 hours (37° C., 5% $CO_2$) before being assayed for viability using the colorimetric MTT assay (Mosmann (1983) J. Immunol Methods 65: 55–63). $EC_{50}$ values (cytotoxic concentrations for 50% of cells in culture) were calculated for MTX and DP-MTX-71 in the presence and absence of Leucovorin.

TABLE 3

Effects of MTX and DP-MTX-71 on cell growth in the presence and absence of leucovorin

| Compound | Cell line | $EC_{50}$, nMol No Leucovorin | $EC_{50}$, nMol + 10 µM Leucovorin |
|---|---|---|---|
| MTX | CEM | 23 ± 13 | 910 ± 378 |
| MTX | CEM-MTX | 2535 ± 224 | 19965 ± 12807 |
| DP-MTX-71 | CEM | 182 ± 75 | 1817 ± 639 |
| DP-MTX-71 | CEM-MTX | 225 ± 49 | 5798 ± 3939 |

As can be seen from the results summarized in Table 3, the cytotoxic effect of DP-MTX-71 on the wild type and MTX-resistant human tumor cell lines was greatly reduced (10- and 26-folds, respectively) in the presence of the reduced folate Leucovorin. The fact that leucovorin presence interferes with the cytotoxic effect of DP-MTX-71 is an indication that the drug inhibits the activity of dihydrofolate reductase (DHFR).

These results indicate that DP-MTX-71 inhibits DHFR, hence suggesting that it functions as a classical antifolate.

Example 7

Effect of DP-MTX-71 on $PLA_2$

DP-MTX-71 was evaluated for inhibition of phospholipase $PLA_2$-I and $PLA_2$-II activities (PanLab catalog # 160000 and 160100, respectively). Phospholipase $PLA_2$ activity was assayed in vitro as described by Katsumata et al. (Anal. Biochem. (1986) 154: 676–681) in the presence of 0.3, 3, 30 and 300 µM DP-MTX-71. $IC_{50}$ values, namely the concentration of the tested compound that inhibits 50% of the enzyme activity, were calculated.

Greater than 50% inhibition was observed for the inhibition of $PLA_2$-I ($IC_{50}$~28 µM). Moderate activity (41% inhibition at 300 µM) was also noted for inhibition of $PLA_2$-II. These values are well within the range of $IC_{50}$ values calculated for other known inhibitors of PLA2; NDGA and Quinacrine ($IC_{50}$ values 40 µM and 390 µM, respectively).

The fact that DP-MTX-71 inhibits $PLA_2$ indicates that the DP-MTX molecule may serve as a substrate for this enzyme.

Example 8

Effect of DP-MTX-71 on Various Tumor Cell Lines

The cytotoxic effect of DP-MTX-71 was evaluated on various tumor cell lines as indicated in Table 3 below. The cultured cells were incubated, during their linear growth phase, in the presence of increasing concentrations of either commercial MTX or the DP-MTX-71 derivative. Cell viability was analyzed after 72 hours incubation (37° C., 5% $CO_2$) using the colorimetric MTT assay (Mosmann (1983) J. Immunol Methods 65: 55–63). $EC_{50}$ values were calculated from the dose response curves and are summarized in Table 4.

TABLE 4 cytotoxic effect of DP-MTX-71 on various tumor cell lines

| Name of cell line | MTX $EC_{50}$, nMol | DP-MIX-71 $EC_{50}$, nMol | Source |
|---|---|---|---|
| CEM | 21 | 169 | T-cell ALL (human) |
| C6 | 46 | 14 | Glioma (rat) |
| Jurkat | 21 | 162 | T-cell lymphoma |
| Du148 | 29 | 16 | Prostate cancer (human) |
| J774 | 112 | 22 | Myeloma (mouse) |
| L1210 | 13 | 206 | lymphocytic leukemia (mouse) |
| N87 | 13486 | 2332 | Gastric carcinoma (human) |
| A431 | 850 | 737 | Colon adenocarcinoma (human) |
| T47D | 50000 | 23503 | Mammary cancer (human) |

As can be seen from the results presented in Table 4, the cell growth inhibitory effects of MTX and DP-MTX-71 greatly varied depending on the tested tumor cell line. MTX was found to be more effective than DP-MTX-71 in inhibiting cell growth of CEM, Jurkat and L1210 cell lines. On the other hand, DP-MTX-71 was more effective in inhibiting cell growth of C6 glioma, J774 myeloma and N87 carcinoma cell lines.

Example 9

DP-MTX-71 Overcomes Multi-drug Resistance (MDR)

In order to further characterize the activity of DP-MTX-71, the cytotoxic effect of the compound was measured on cell cultures of drug resistant mutants derived from the mouse tumor cell line L1210.

Three cell lines were employed: the parent leukemia cell line which is sensitive to methotrexate (L1210), RFC-mediated MTX-resistant cell line (L1210-MTX), and a double mutated cell line which is resistant to MTX and Taxol (L1210-MTX-TAX). The Taxol resistance is MDR-mediated, due to increased activity of the P-glycoprotein (P-gp) pump. Cell death was tested using the MTT assay. EC50 values were calculated and the results are presented in Table 5.

TABLE 5 cytotoxic effect of DP-MTX-71 on mutant tumor cell lines

| Cell line | MTX $EC_{50}$, nMol | DP-MTX-71 $EC_{50}$, nMol | TAX $EC_{50}$, nMol |
|---|---|---|---|
| L1210 | 14 | 207 | 8 |
| L1210-MTX | 1081 | 255 | 8 |
| L1210-MTX-TAX | 987 | 221 | 1846 |

As shown in Table 5, DP-MTX-71 was found to be more potent than the parent drug MTX in inhibiting cell growth of the MTX-resistant cell lines L1210-MTX, but not of the wild type cell L2120. This result is similar to the results obtained with the human leukemia cell line CEM and the MTX-resistant cell line CEM-MTX. In addition, DP-MTX-71 was found to be about 4–5 times more potent than MTX in inhibiting growth of the double mutant L1210-MTX-TAX that is characterized by increased activity of P-gp.

These results indicate that DP-MTX-71 may overcome multi-drug resistance (MDR).

Example 10

DP-MTX-71 Does Not Provoke MDR Phenotype

An effort was directed towards generation of DP-MTX-71 resistant cell line. The following protocol for mutant selection was followed. Exponentially growing Chinese hamster ovary (CHO) AA8 cells in monolayer conditions were washed with PBS, trypsinized and plated (300,000 cells/T25 flask) in alpha MEM medium (Beth Haemek, Israel) containing 5% fetal calf serum, penicillin/streptomycin and 2 mM glutamine. DP-MTX-71 (from a 1 mM stock) was added at a 50 nM concentration at the time of cell seeding. Ten to fourteen days later, when cells doubled their density, the attached cells were washed with PBS, trypsinized, viability counted, and plated as above in the presence of 50 nM and 75 nM DP-MTX-71 (50% increment).

This multiple step drug selection was continued by using 25–50% increments in drug concentration over a period of 8 months. Selection was terminated at 1 micromolar DP-MTX-71 concentration.

Only a single resistant cell line was obtained after eight months of repeated passage of the cells under the selective pressure of presence of DP-MTX-71. This period is significantly longer than the time required to obtain cell lines resistant to the parent drug MTX or other known derivatives thereof. The obtained DP-MTX-71 resistant cell line was characterized and was found to acquire resistance by over-expressing the target enzyme DHFR. It is important to note that DP-MTX-71 did not induce over-expression of P-gp. This may be an indication that P-gp does not affect DP-MTX-71.

From these results it appears that DP-MTX-71 has a potential to serve as a cytotoxic agent that lacks or has a reduced ability to provoke multi-drug resistance (MDR).

Example 11

Effect of DP-MTX on Survival of Tumor Bearing Mice (Viability Studies)

The anti-tumor effects of DP-MTX were evaluated in vivo on mice transplanted with L1210 murine leukemia cells.

Mice of strain B6D2F 1/J (stock number 100006), which are F1 cross of C57/BJ×DBA/2J, were purchased from The Jackson Laboratory (JAX Mice & Mouse Model Related Services, NH, USA). Animals were allowed 10 days adjustment time at our animal care facility before initiation of the experiment.

Mice were transplanted with $1 \times 10^6$ L1210 (mouse leukemia; ATCC# CCL-219) or L1210MTX (RFC-mediated MTX resistant L1210 mutant; provided by Dr. Y. Assraf, Technion, Israel) cells by injection into the peritoneum (i.p.) (day 1). Two days later (on day 3) groups of animals (8 mice per group) were injected i.p. with either 3 mg/Kg commercial MTX (Abitrexate®, from ABIC, Israel) or molar equivalent dose of DP-MTX-71. Another group of 8 animals were injected with vehicle solution (2% propylene-glycol, 0.2% Tween-80 in PBS) and serve as control group. Thereafter, the same doses of MTX or DP-MTX-71 (MTX equivalent dose) or vehicle only, were injected i.p. every two days until day 17. Mice survival was monitored daily until the end of the experiment on day 21.

As shown in FIG. 1, mice implanted i.p. with tumors died after about 10 days. MTX treatment, which by itself caused no mortality in the mice, effectively prolonged the life of mice implanted with tumors; in this case animal death started on day 15. Treatment with DP-MTX-71 was the most effective, and prolonged survival of animals transplanted with L1210 tumor cells for at least 7 days beyond survival of animals treated with MTX. At the end of the experiment, on day 21, only one mouse (out of 8 mice) survived in the control group or in the group treated with MTX, in comparison to five mice (out of 8) survived in the group treated with DP-MTX-71.

Similar trend (results not shown) was observed in the experiment where the mice were transplanted with L1210/MTX cells (tumor cell line resistant to MTX). In this case treatment with 3 mg/Kg dose equivalent DP-MTX-71 prolonged animal survival by 3 days beyond survival of animals treated with MTX. Furthermore, a dose dependent effect of DP-MTX-71 was observed. Prolongation of animal survival for 17 days beyond survival of animals treated with MTX was observed for 50% of the mice treated with 10 mg/Kg dose equivalent of DP-MTX-71 (i.p. injected every 4 days).

These results indicate that DP-MTX-71 is more effective than the patent drug MTX in increasing life span of tumor bearing mice.

Example 12

Effect of DP-MTX in Preventing Tumor Growth (In Vivo)

Protection against tumor growth was examined in mice pretreated with MTX or DP-MTX-71.

Female B6D2Fl/J mice were injected i.p. with either 3 mg/Kg commercial MTX (6 animals in a group) or equivalent dose of DP-MTX-71 (8 animals in a group) on every other day for a period of 21 days. At the end of this regimen, the mice were injected with $1 \times 10^6$ L1210 cells into the peritoneum. The animals were then monitored for viability for 12 days subsequent to the injection of the tumor cells. As can be seen in Table 6, at the end of the experiment, namely 12 days after the injection of the tumor cells, 2 and 5 animals survived in the groups treated, respectively, with MTX and DP-MTX-71.

TABLE 6

Effect of DP-MTX on survival of mice implanted with L1210 tumor cells

| Days after tumor implantation | Surviving mice (MTX pre-treatment) | Surviving mice (DP-MTX-71 pre-treatment) |
| --- | --- | --- |
| 9 | 6/6 | 8/8 |
| 10 | 4/6 | 8/8 |
| 11 | 3/6 | 8/8 |
| 12 | 2/6 | 5/8 |

DP-MTX derivative shows an improved pharmacokinetic properties comparing to the parent drug MTX. Pre-treatment with DP-MTX-71 was effective in increasing survival of mice implanted with tumor cells.

Example 13

Anti-inflammatory Activity of DP-MTX (in the Carrageenan-induced Rat Paw Oedema Model)

The potential anti-inflammatory activities of various DP-MTX prodrugs are evaluated by employing the experimental model of carrageenan-induced paw oedema in the rat.

Carrageenan-induced rat paw edema is a widely employed animal model for acute inflammation. The objective of the study is to assess the potential prophylactic effects of DP-MTX derivatives on the prevention of inflammatory swelling and, in particular, to compare the efficacy parameters with those obtained for MTX. The experimental set-up is as follows: Male Sprague-Dawley rats weighing 120–180g (supplied by Harlan Laboratories Breeding Center, Israel) are intraperitoneally (i.p.) injected with MTX or DP-MTX one hour prior to the induction of inflammation with carrageenan. MTX and the tested MTX-derivatives are applied at a dose level of 1 mg/kg body weight. Animals injected with the vehicle only serve as a control group.

Paw edema is induced by a single sub-plantar injection of 0.1 ml 2% carrageenan in physiological saline, into the right hind paw of each test animal. Just prior to paw edema induction, the paw thickness of the test animals'right hind paws is measured in duplicate using a plethysmograph and micrometer to provide a baseline. At 3, 5 and 7 hours post carrageenan injection, the right paw thickness is measured in the same manner as before.

The assessment of potential anti-inflammatory activity is based on the relative reduction (%) in mean group values of carrageenan-induced right hind paw edema in animal groups treated with tested compounds versus respective values in the control group treated with vehicle only. The effect of DP-MTX on carrageenan-induced paw edema is evaluated in comparison to the effect of methotrexate by following severity of inflammation as determined by hind paw swelling.

Studies of this kind indicate that the phospholipid derivatives of methotrexate have higher therapeutic indices compared to methotrexate in the carrageenan-induced paw edema model for inflammation.

Example 14

Effect of DP-MTX-71 in Collagen Arthritis Inflammation Model

The potential effect of DP-MTX-71 in treatment of arthritis was examined in collagen arthritis model of inflammation in mice.

Groups of 5 Balb/cByJ mice strain, 6–8 weeks of age, were used for the induction of arthritis by monoclonal antibodies (mAbs) plus lipopolysaccharide (LPS). The animals were administered intravenously a combination of 4 different mAbs (PanLab's protocol # 553600) in total of 4 mg/mouse (day 0), followed by intravenous 25 μg of LPS 72 hours later (day 3). From day 3, one hour after LPS administration, DP-MTX-71 (30 mg/kg) was administered orally once daily for 3 consecutive days. Animals treated with vehicle serve as control group. Paw edema was monitored by using a plethysmometer for measuring paw volume of the two hind paws on day 0, 5, 7, 10, 14 and 17. Assessment of anti-inflammatory activity was based on the relative reduction (%) in hind paw swelling in animals treated with tested compound in comparison to the control group treated with vehicle only. Results: significant reduction of hind paws swelling of 22%, 27%, 27% and 30% was noted on days 5, 7, 10 and 17, respectively. DP-MTX-71 shows anti-inflammatory activity as demonstrated in the collagen arthritis animal model.

Example 15

In Vivo Efficacy and Toxicity Studies of DP-MTX (in Rat Adjuvant-induced Arthritis)

DP-MTX compounds were evaluated for efficacy and toxicological profile in the progression of adjuvant-induced arthritis (AA) in Lewis rats, which is a widely employed animal model for the human rheumatoid arthritis (RA). The effects of DP-MTX were compared with those obtained with MTX.

Arthritis was induced in the left hind paws of male Lewis rats by sub-plantar injection of a suspension of *Mycobacterium butyricum* in paraffin oil. Test animals were intraperitoneally (i.p.) injected with either 0.02 mg/kg or 0.1 mg/kg of DP-MTX prodrug or the commercially available methotrexate (Abitrexate®). Dosing was initiated on the day of AA induction and thereupon continued as once-a-day repeated injections throughout a 3-week study period. An additional group of rats was treated with solvent only (1% propylene glycol and 0.01% Tween-80 in USP water) and served as a control group.

Assessment of the DP-MTX effects was based on relative changes in hind paw thickness, measured prior to the treatment, during and at termination of the study period. These effects were compared to the respective effects of MTX. Determination of body weight gain at study termination was used as a measure of general systemic anti-inflammatory activity. In addition, all tested animals were inspected for clinical signs (e.g. histopathological patterns in the spleen, liver and intestines) to evaluate toxicity.

Results indicate that phospholipid derivatives of methotrexate are effective in suppression of AA-induced inflammatory phenotypes such as swelling, and evoke less pathological events.

Example 16

In Vivo Efficacy Studies of DP-MTX (in the Experimental Allergic Encephalomyelitis (EAE) Model System)

The effects of DP-MTX compounds on sites of inflammation within the central nervous system are assessed in an animal model. The chosen model system is experimental allergic encephalomyelitis (EAE) which is a known animal model for multiple sclerosis (MS).

In a preliminary set of experiments EAE was induced in SJL/J mice by either one of two schemes: a) active induction by injecting mice via the footpads with proteolipid protein ($PLP_{139-151}$) emulsified in complete Freund's adjuvant (CFA) as described by Weinberg et al. (J. Immunol. (1999) 162: 1818–1826), or b) passive induction, namely adoptive transfer of EAE accomplished by transferring reactive cells from a donor. Briefly, PLP-reactive lymph node cells are drawn from mice inoculated with PLP-CFA, 10 days post inoculation. The cells are incubated in vitro for 4 days with soluble PLP, then collected, washed and transferred to naive mice.

The tested DP-MTX compounds are injected either i.p or i.v. at 8, 10 or 12 days post inoculation in the case of the active induction of EAE, or at days 2, 4 and 6 after cell transfer in the passive induction protocol. According to both procedures, the animals are sacrificed 4 hours after injection of the tested DP-MTX compound. Blood samples are collected and the animals' brains and spinal cords are excised and homogenized. The levels of MTX in serum and tissue extracts of the treated animals are determined. Briefly, samples of brain or spinal cord are suspended in three volumes of 5 mg/ml sodium ascorbate. Samples are homogenized, sonicated and centrifuged at 27000 g for 30 min. Supernatants are placed in boiling water bath for 10 min. and then centrifuged at 3000 g for 1 min. The obtained clear supernatants are used for determination of free MTX. Abbot's TDX method and kit are used to determine the levels of MTX in serum and tissue extracts.

A group of mice with EAE are kept for a longer time while receiving leucovorin daily and is watched for EAE symptoms.

EAE severity is evaluated statistically by following two main parameters:
a) neurological symptoms scored according to a standard score in which: 0- no clinical signs; 1- limp tail; 2- ataxia; 3- hind limb paralysis; 4- complete paralysis and incontinence; 5- moribund and death; and
b) histopathological symptoms which are evaluated by using sections of the brain stained with hematoxylin-eosin for detection of mononuclear cell infiltration and with luxol-fast for the detection of demyelination.

Results have shown that the tested DP-MTX compounds reach the site of inflammation and exert their therapeutic effect in inhibiting the clinical signs of EAE.

Thus, DP-MTX may be useful in treatment of CNS autoimmune diseases and inflammation.

Example 17

Effects of DP-MTX and DP-5FUdR Compounds in Restenosis Model System in Rats.

The anti-proliferative effects of compounds of the invention are assessed in a model system for restenosis in rats. Restenosis is a phenomenon of neointimal formation occurring following percutaneous transluminal coronary angioplasty (PTCA) procedures.

Experimental neointimal formation is induced by balloon injury in rats according to the following procedure. Male Sprague-Dawley rats (380–450 g) are anesthetized by inhalation of halothane and dinitric oxide. After the right common carotid artery and the right external carotid artery are exposed, a 2F Fogarty arterial embolectomy catheter (Baxter Healthcare, Santa Ana, Cailf. is inserted into the lumen of the right external carotid artery and is guided to a fixed distance (about 5 cm). The balloon is inflated with saline and is withdrawn at a constant rate back to a point proximal to the site of insertion. This procedure is repeated three times.

The effect of the balloon injury is assessed 2 to 4 weeks following the above-described treatment. The left (control untreated) and right (experiment, treated) carotid arteries of rats under pental overdose, are perfused in situ with 4% formaline, pH 7.4 and then excised. Each of the left and right arteries is cut at three segments: upper, middle and lower, and then fixed in formaline. Cross-sections are stained with van Gieson's stain and the intima and media thickness is evaluated under a microscope. A higher calculated ratio of intima/media in the treated (right) artery in comparison to the control (left) artery, is an indication of neointimal formation and development of restenosis.

Various DP-MTX and DP-5-FUdR compounds are tested for preventive and/or curative effects on restenosis by carrying-out the following schemes:
a) Preventive procedure—the tested compound is daily administered starting from 7 to 3 days prior to the induced balloon injury, and up to the day of the induced injury.
b) Curative procedure—the tested compound is daily administered starting from the day of induced balloon injury and up to 14 to 30 days after the induced injury.
Peroral- and parenteral-, such as subcutaneous, modes of administration may be employed in both the preventive and curative procedures.
In yet another regimen, a combination of the preventive and the curative procedures is tested in the rat model system for restenosis.

Both DP-MTX and DP-5-FUdR compounds are promising agents for inhibition of intimal proliferation and may be useful in clinical procedures.

While the present invention has been particularly described, persons skilled in the art will appreciate that many variations and modifications can be made. Therefore; the invention is not to be construed as restricted to the particularly described embodiments, rather the scope, spirit and concept of the invention will be more readily understood by reference to the claims which follow.

What is claimed is:

1. A prodrug of the general formula I

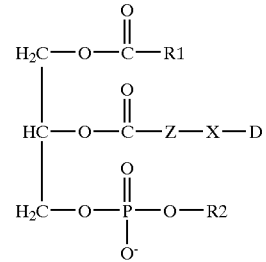

Formula I or a pharmaceutically acceptable salt thereof, wherein:

R1 is a saturated or unsaturated, straight-chain or branched, substituted or unsubstituted hydrocarbon chain having from 2 to 30 carbon atoms;

R2 is H or a phospholipid head group;

Z is saturated or unsaturated, straight-chain or branched, substituted or unsubstituted hydrocarbon chain having from 2 to 15 carbon atoms, which may include cyclic elements and is optionally interrupted by one or more atoms selected from oxygen and sulfur atoms;

X is a direct covalent bond or selected from the group consisting of O, S, NH and C(O) groups; and D is the residue of an anti-proliferative drug, and wherein the anti-proliferative drug is methotrexate or pharmaceutically acceptable derivatives thereof, wherein the bound anti-proliferative drug residue is an inactive form of the drug which is selectively activated in cells and tissues with elevated phospholipase activity.

2. The prodrug according to claim 1, wherein an ester bond at position sn-2 of the phospholipid of the general formula I is cleaveable by a lipase.

3. The prodrug according to claim 2, wherein said phospholipase is phospholipase $A_2$ ($PLA_2$).

4. The prodrug according to claim 1, wherein R1 is an hydrocarbon chain having from 5 to 20 carbon atoms.

5. The prodrug according to claim 1, wherein R1 is an hydrocarbon chain having 15 or 17 carbon atoms.

6. The prodrug according to claim 1, wherein R2 is selected from the group consisting of choline, ethanolamine, inositol and serine.

7. The compound according to claim 1 selected from the group consisting of:

1-Stearoyl-2-[3-[α-MTX amido)-Propanoyl]-sn-Glycero-3-phosphocholine,

1-Stearoyl-2-[3-[γ-dodecylate-α-MTX amido)-Propanoyl]-sn-Glycero-3-phosphocholine, 1-Stearoyl-2-[4-(α-MTX amido)-Butanoyl]-sn-Glycero-3-phosphocholine, 1-Stearoyl-2-[6-(α-MTX-amido)-Hexanoyl]-sn-Glycero-3-phosphocholine, 1-Stearoyl-2-[8-(α-MTX-amido)-Octanoyl]-sn-Glycero-3-phosphocholine, and 1-Stearoyl-2-[3-(α-dodecylate-γ-MTX-amido)-Propanoyl]-sn-Glycero-3-phosphocholine.

8. The prodrug according to claim 1, which is 1-Stearoyl-2-[3-[α-MTX amido)-Propanoyl]-sn-Glycero-3-phosphocholine.

9. The prodrug according to claim 1, which is 1-Stearoyl-2-[3-(α-dodecylate-γ-MTX-amido)-Propanoyl]-sn-Glycero-3-phosphocholine.

10. The prodrug according to claim 1, wherein the methotrexate is bound into Formula I at the α-carboxyl group of methotrexate.

11. The prodrug according to claim 1, wherein the methotrexate is bound into Formula I at the γ-carboxyl group of methotrexate.

12. A pharmaceutical composition comprising, as an active ingredient, a prodrug of the general formula I according to claim 1 and a pharmaceutically acceptable carrier.

13. The pharmaceutical composition according to claim 12, further comprising an additional neoplastic agent.

14. The pharmaceutical composition according to claim 12, which is suitable for oral, ocular, nasal, parenteral, topical or rectal administration.

15. The pharmaceutical composition according to claim 12, which is suitable for oral administration, intravenous administration or topical administration.

16. The pharmaceutical composition according to claim 12, in the form of solutions, suspensions, capsules, tablets, aerosols, gels, ointments or suppositories.

17. A method of manufacturing a medicament which comprises combining a prodrug of the general formula I according to claim 1 or a pharmaceutically acceptable salt thereof and a pharmaceutically acceptable carrier.

18. A method for treatment of a disease or disorder related to an inflammatory condition comprising administering to a patient in need thereof a therapeutically effective amount of a pharmaceutical composition according to claim 12.

19. The method according to claim 18, wherein said disease or disorder related to an inflammatory condition is selected from the group consisting of granulomatous diseases, arthritis, rheumatoid arthritis, multiple sclerosis, systemic sclerosis, systemic sclerosis, asthma, psoriasis, systemic lupus erythematosus, inflammatory bowel syndromes and migraines.

20. A method for treatment of a disease or disorder according related to a degenerative or atrophic condition comprising administering to a patient in need thereof a therapeutically effective amount of a pharmaceutical composition according to claim 12.

21. The method according to claim 20, wherein said disease or disorder related to a degenerative or atrophic condition is a central or peripheral neurological disease or disorder.

22. The method according to claim 20, wherein said disease or disorder related to a degenerative or atrophic condition is selected from the group consisting of autoimmune, cerebrovascular and neurodegenerative diseases and disorders such as idiopathic dementia, vascular dementia, multi-infarct dementia, traumatic dementia, Alzheimer's disease, Pick's disease, Huntington's disease, dementia paralitica, Parkinson's disease, diabetic neuropathy, amyotrophic lateral sclerosis, ischemia of the optic nerve, age-related macular degeneration, stroke and ischemia.

23. A method for treatment of a disease or disorder related to uncontrolled cell growth comprising administering to a patient in need thereof a therapeutically effective amount of a pharmaceutical composition according to claim 12.

24. The method according to claim 23, wherein said disease or disorder related to uncontrolled cell growth is a neoplastic growth.

25. The method according to claim 24 wherein said neoplastic growth is a primary or a secondary tumor.

26. The method according to claim 24 wherein said neoplastic growth is a drug-resistant tumor.

27. The method according to claim 24 wherein said neoplastic growth is a methotrexate-resistant tumor.

28. The method according to claim 24 wherein said neoplastic growth is a multidrug-resistant tumor.

29. The method according to claim 23, wherein said disease or disorder related to uncontrolled cell growth is selected from the group consisting of psoriasis, lymphocytic leukemia, myelogenous leukemia, Burkitt's lymphoma, non-Hodgkin's lymphomas, mycosis fungoides, osteosarcoma, hydatidiform mole, trophoblastic diseases such as chorioadenoma destruens and choriocarcinoma, and carcinomas of the head and neck, breast, liver, lung, colon, ovary, cervix, urinary, bladder, prostate, pancreas, skin, the gastrointestinal tract and the oropharyngeal areas.

* * * * *